United States Patent [19]

Dugan et al.

[11] 4,456,688

[45] Jun. 26, 1984

[54] MICROBIOLOGICAL DESULFURIZATION OF COAL

[75] Inventors: Patrick R. Dugan, Columbus; William A. Apel, Cincinnati, both of Ohio

[73] Assignee: The Ohio State University, Columbus, Ohio

[21] Appl. No.: 929,214

[22] Filed: Jul. 28, 1978

[51] Int. Cl.$^3$ .................... C07G 17/00; C10G 32/00
[52] U.S. Cl. .................... 435/267; 435/262; 435/282
[58] Field of Search .............. 195/2, 3, 3 H; 435/262, 435/267, 282

[56] References Cited

U.S. PATENT DOCUMENTS

| | | | |
|---|---|---|---|
| 2,636,823 | 4/1953 | de Becze | 195/111 |
| 3,105,014 | 9/1963 | Harrison | 195/3 |
| 3,455,679 | 7/1969 | Mayling | 75/101 |
| 3,649,459 | 3/1972 | Wolnak et al. | 195/96 |
| 3,843,464 | 10/1974 | Usami et al. | 195/2 |
| 3,871,956 | 3/1975 | Azarowies | 195/2 |
| 3,982,995 | 9/1976 | Yen et al. | 195/3 H |

OTHER PUBLICATIONS

Dugan, P. R., C. B. Macmillan, and R. M. Pfister, J. Bacteriol., 101, 973, 982, (1970).
Tuttle, J. H., C. I. Randles, and P. R. Dugan, J. Bacteriol., 95, 1495, (1968).
Tuttle, J. H., P. R. Dugan, C. B. Macmillan, and C. I. Randles, J. Bacteriol., 97, 594 (1969).
Bohlool, B. B., and T. D. Brock, Appl. Microbiol., 28, 11, (1974).
Belly, R. T., and T. D. Brock, J. Bacteriol., 117, 726, (1974).
Joseph, J. M., Ohio J. Sci., 53, 123, (1953).
Lorenz, W. C., and E. C. Tarpley, U.S. Bureau of Mines Rept., No. 6247, U.S. Dept. Interior, 13 pp., (1963).
Lau, C. M., K. S. Shumate, and E. E. Smith, Proceed 3rd Symp. on Coal Mine Drainage. Mellon Inst., Pittsburgh, PA., p. 114, (1970).
Remsen, C. C., and D. G. Lundgren, Bacteriol. Proc., 33, (1963).
Shafia, F., R. F. Wilkinson, J. Bacteriol., 97, 256, (1969).
Shafia, F., K. R. Brinson, M. W. Heinzman, and J. M. Brady, J. Bacteriol., 111, 56, (1972).
Shumate, et al., Rept. U.S. Environ. Protection Agency, Water Poll. Control Ser. DAST-42, 14010 FPR. Washington, D.C., (1971).
Tabita, R., and D. G. Lundgren, J. Bacteriol., 108, 328, 334, (1971).
Apel, W. A., P. R. Dugan, J. A. Filppi, and M. S. Rheins, App. Environ, Microbiol., 32, 159, (1976).
Capes, C. E., A. E. McIlhinney, A. f. Sirianni, and I. E. Puddington, Canadian Mining and Metallurgical Bull., 88-91, (1973).
Temple, K. L., and W. A. Kohler, Res. Bull., No. 25, Engineering Experiment Station, Univ. of W. Va., Morgantown, (1954).
Borichewski, R. M., J. bacteriol., 93, 597-599, (1967).
Dugan, P. R., Ohio J. Sci., 75, 266, (1975).
Schnaitman, C., and D. G. Lundgren, Can. J. Microbiol., 11, 23, (1965).
Tuttle, J. H., and P. R. Dugan, can. J. Microbiol., 22, 719, (1976).
Tuttle, J. H., P. R. Dugan, and W. A. Apel, Appl. and Environ. Microbiol., 33, 459-469, (1977).
Singer, P. C., and W. Stumm, Science, 167, 1121, (1970).
Gary et al., Research and Develop. Rept., No. 77, U.S. Dept. Interior, 99 pp., (1973).
Colmer, A. R., and M. E. Hinkle, Science, 106, 253, (1947).
Colmer, A. R., K. L. Temple, and M. E. Hinkle, J. Bacteriol., 59, 317, (1949).
Dugan, P. R., "Biochemical Ecology of Water Pollution", pp. 123-137, Plenum Publ. Co., N.Y., N.Y., (1972).
Duncan, D. W., J. Landesman, and C. C. Walden, Can. J. Microbiol., 13, 397, (1967).
Leathan, W. W., S. A. Braley, and L. D. McIntyre, Appl. Microbiol., 1, 61-64. Appl. Microbiol., 1, 65-68, (1953).
Temple, K. L., and E. W. Delchamps, Appl. Microbiol., 1, 255-258, (1953).
Silverman, M. P., M. H. Rogoff, and I. Wender, Appl. Microbiol., 9, 491-496, (1961).

Silverman, M. P., M. H. Rogoff, and I. Wender, Fuel, 42, 113, (1963).
Sutton, J. A., and J. D. Corrick, U.S. Bu. Mines Rept., 5839, (1961).
Vogler, K. G., and W. W. Umbreit, Soil Sci., 51, 331, (1941).
Ford, W. H., H. K. Roffman, W. A. Beimborn, Combustion, p. 36, (Aug. 1977).
Roffman, H., Digest of Technical Papers, 1974 Earth, Environ. and Resource Conf., p. 106, (1974).
Ashmead, Colliery Guardian, 190, 694–698, (1955).

*Primary Examiner*—Alvin E. Tanenholtz
*Attorney, Agent, or Firm*—Millard & Cox

[57] ABSTRACT

A method for reducing the sulfur content of coal wherein comminuted coal is contacted with an enrichment culture which contains acid tolerant Thiobacillus species in combination with acid tolerant hetrotrophic microorganisms in an amount effective to act in a symbotic or synergistic manner with the Thiobacillus species. The initial pH of the coal culture combination may be selected so as to enhance the development of a commercially practical rate of sulfur removal.

27 Claims, 12 Drawing Figures

MICROBIOLOGICAL DESULFURIZATION OF COAL

BACKGROUND

The return of industry to the utilization of coal as a principal energy source has considerably heightened efforts at developing non-air polluting techniques for its combustion. While coal resources are plentiful, the quality thereof vis-a-vis non polluting combustability varies from region to region. Coal quality, from the standpoint of air quality standards, is predicated principally upon the sulfur and nitrogen content thereof. Concerning the former, generally there are three (3) forms of sulfur in coal: (a) organic sulfur in which the sulfur is covalently bonded to carbon in the general forms —R—S—S—R, and —R—S—R— or bound as sulfate in the general form R—O—SO$_3$; (b) pyritic sulfur in the form iron pyrite and marcasite, both of which have the same chemical combination, FeS$_2$, but differ in crystalline structure; and (c) sulfate. Of the above three forms of sulfur, the sulfate content witnessed is very low and of minor importance, while the pyritic sulfur content of coal will range from about $\frac{1}{2}\%$ to 4% and generally is present in an amount exceeding the content of organic sulfur in coal.

Criteria developed under the authority of the Clean Air Act Amendments of 1970 (Pub. L. 91-604, Dec. 31, 1970, 84 Stat. 1676) have provided a limit on the amount of SO$_2$ permitted in ambient air of 0.03 ppm (80 $\mu$g/m$^3$) as an annual arithmetic mean concentration. A 24 hour maximum limit of 9.14 ppm (365 $\mu$g/m$^3$) not to be exceeded more than once each year also was established. Such criteria can be construed to restrict the combustion of coal at large power plants without scrubbers to utilization of coal which contains somewhere between 0.5% and 1.5% total sulfur. Coal of less than 1% total sulfur generally is considered "low sulfur coal" and coal with greater than about 1.5% to 2.0% total sulfur considered by governmental authorities to be "high" sulfur coal.

The importance of developing a technique for improving coal by lowering the sulfur content thereof prior to combustion becomes apparent in view of estimations that approximately 33% of the coal available in the continental United States exhibits a sulfur content acceptable for combustion without scrubbers. Further in this regard, 62% of the low-sulfur coal reserves in the continental United States are found west of the Mississippi River. Unfortunately, almost 90% of the electric power generating capacity utilizing coal as a heat source is located east of the Mississippi River. See in this regard the following publication:

I Gary, J. H., R. M. Baldwin, C. Y. Bao, M. Kirchner, and J. D. Golden, Research and Develop. Rept. No. 77 prepared for U.S. Office of Coal Research, U.S. Dept. Interior, 99 pp. (1973).

In 1947 bacteria were discovered in acidic coal mine drainage exhibiting a capacity to derive cellular energy requirements from the oxidation of the Fe$^{+2}$ portion of iron pyrite. These bacteria ultimately were to be designated as *T. ferrooxidans.* See in this regard:

II Colmer, A. R. and M. E. Hinkle. 1947. Role of microorganisms in acid mine drainage: a preliminary report.

Previous to the above publication (II), investigators had known that acidophilic Thiobacilli other than *T. ferroxidans,* notably *T. Thiooxidans* retained a capability for oxidizing reduced sulfur with concomitant production of sulfuric acid. However, with the identification of *T. ferroxidans,* investigators developed an interest in its used in connection with the beneficiation of high pyrite coal.

Looking to the oxidation of the chemically reduced compound FeS$_2$ (pyrite), exposure to oxygen and water results in oxidation of the FeS$_2$ through a complex series of chemical reactions which are summarized as follows:

$$Fe^{+2} \rightarrow Fe^{+3} + electron \tag{1}$$

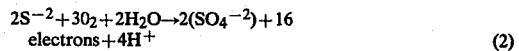

$$2S^{-2} + 3O_2 + 2H_2O \rightarrow 2(SO_4^{-2}) + 16\ electrons + 4H^+ \tag{2}$$

$$\text{Sum: } FeS_2 + 3O_2 + 2H_2O \rightarrow 2H_2SO_4 + Fe^{+3} \tag{3}$$

The oxidized iron (Fe$^{+3}$) formed, subsequently reacts with water to produce ferric hydroxide and more acid according to the following equation:

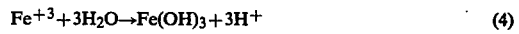

$$Fe^{+3} + 3H_2O \rightarrow Fe(OH)_3 + 3H^+ \tag{4}$$

In connection with the above reactions, reference is made to publication II above as well as the following additional publictions:

III Colmer, A. R., K. L. Temple, and M. E. Hinkle, J. Bacteriol., 59, 317 (1949).

IV Dugan, P. R., "Biochemical Ecology of Water Pollution", pp. 123-137, Plenum Publ. Co., N.Y., N.Y. (1972).

V Duncan, D. W., J. Landesman, and C. C. Walden, Can. J. Microbiol., 13, 397 (1967).

VI Leathan, W. W., S. A. Braley, and L. D. McIntyre, Appl. Microbiol., 1, 61-64. Appl. Microbiol., 1, 65-68 (1953)

As may be expected, prior to the return of interest on part of industry to the utilization of coal as a principal fuel, the concern of investigators was somewhat devoted to control over acidic coal mine drainage, i.e., the formation of sulfuric acid from pyrite. See publication VI above as well as the following:

VII Temple, K. L. and E. W. Delchamps, App. Microbiol., 1, 225-258 (1953).

Subsequent investigations into the activity of acidophilic iron and sulfur oxidizing bacteria in conjunction with the removal of pyrite in coal are described, for example, in the following publication:

VIII Ashmead, D., Colliery Guardian, 190, 694-698 (1955).

The latter publication describes an effort demonstrating that the natural microbial flora of acidic mine waters increases the rate of oxidation of pyrite in a 4% pyrite sulfur sample compared to oxidation in the absence of added bacteria. Subsequent to the above effort, it was reported that Ferrobacillus (presently *T. ferrooxidans*) accelerated the oxidation of samples of pyrite and coarsely crystalline marcasite extracted from coal (greater than 60% pyrite content) but that the cells were inactive on coarsely crystalline iron pyrite. Oxidation rates in the presence of *T. ferrooxidans* were increased by reducing the pyrite particle size, while *T. thiooxidans* cells were found to be inactive on all the pyritic samples examined. See the following publication:

IX Silverman, M. P., M. H. Rogoff, and I. Wender, Appl. Microbiol. 9, 491-496 (1961).

Of course, investigators have for some time engaged in investigations concerning metallurgical leaching where oxidation of sulfide mineral releases a commercially useful metal ion from an ore. The metal ions generally are recovered from the ensuing acid leachate. Typical efforts in this field are described, for example, U.S. Pat. No. 3,455,679. Commercial scale data concerning bacetrial removal of pyrite from coal appears in publication X below. In that investigation, various percentages of weathered coal were blended as inoculum of bacteria with run of mine (r.o.m.) coal. The investigators reported that an addition of 10% weathered coal resulted in a reduction in the sulfur content of r.o.m. coal from 6.1% to 2.7% during subsequent agglomeration of pyrite from pulverized coal. A flotation technique was utilized in the investigation.

X Capes, C. E., A. E. McJLHinney, A. F. Sirianni, and I. E. Puddington, Canadian Mining and Metallurgical Bull., 88–91 (1973).

Investigators have further speculated that the primary role of bacetria in pyrite oxidation is the production of ferric ions and that those ferric ions produced oxidize more pyrite with the comcomitant regeneration of ferrous ions in accordance with the following equation:

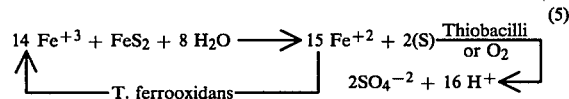

(5)

This microbiological process is analogous to a chemically catalyzed reaction process. That is, living bacteria are oxidation catalysts promoting the oxidation of insoluble metallic sulfate to soluble sulfate, which is then removed by leaching. The bacteria utilize the pryite nutritionally and grow in the system. Speculation as to the validity of the process of the reaction (5) stemmed from reports, as at publication VI above, that iron oxidizing bacteria are more active than the exclusively sulfur oxidizing bacteria relative to rates of pyrite oxidation, particularly in view of earlier observations that ferric sulfate could oxidize pyrite, as set fourth in the following publication:

XI Temple, K. L., and W. A. Kohler, Res. Bull No. 25 Engineering Experiment Station, Univ. of West Virginia, Morgantown (1954).

From the foregoing, it will be apparent that a microbiological process reducing the sulfur content of coal to an extent permitting its non-polluting combustion might be achieved. However, to the present time no commercially promising technique has been developed. Two characteristics of the acidophilic Thiobacilli derogate from their otherwise advantageous capability for reducing pyritic sulfer. These characteristics are: first, the interval of association of the cultures with coal has been considered too extensive to achieve a commercially practical coal pretreatment process; and, secondly, the acidophilic Thiobacilli are known to produce autotoxic metabolic by-products (principally organic acids) which retard further iron and sulfur oxidation by the cells when present in sufficient concentration. Thus without some correction, the process is self defeating. For further discussion of this autotoxic characteristic, reference is made to the following publications:

XII Borichewski, R. M., J. Bacteriol 93, 597–599 (1967).

XIII Dugan, P. R., Ohio J. Sci., 75, 266 (1975).

XIV Schnaitman, C., and D. G. Lundgren, Can. J. Microbiol., 11, 23 (1965).

XV Tuttle, J. H., P. R. Dugan, C. B., Can. J. Microbiol., 22, 719 (1976).

XVI Tuttle, J. H., P. R. Dugan, and W. A. Apel, Appl. and Environ. Microbiol., 33, 459–469 (1977).

In the course of autotoxic activity, lower molecular weight organic acids, particularly alpha-keto acids, some of which are intermediates of the cells' metabolic pathways, inhibit metabolism of iron and sulfur by Thiobacilli by causing the cell membranes thereof to become leaky and ultimately disrupt. As indicated in publication XVI above, this also may allow intolerable amounts of $H^+$ to enter the cell.

SUMMARY

The present invention is addressed to a method for microbiologically removing sulfur from coal. Particularly looking to the removal of pyritic sulfur, the method of the invention utilizes a culture of chemosynthetic autotrophs, for example, acid tolerance Thiobacilli, in symbiotic and/or synergistic combination with acid tolerant heterotrophs, for example, bacteria, yeasts and molds, to achieve sulfur breakdown at commercially practical rates. As one aspect of the symbiotic nature of the cultures utilized, the autotoxic organic acid by-products of the Thiobacillus component of the culture may be metabolically utilized by the acid tolerant heterotrophs of the culture, while the latter serve to provide carbon in the form of carbon dioxide, vitamins, and the like which may be utilized as nutrients for the Thiobacillus component.

As another object and feature of the invention, the pH level of the cultures may be adjusted at the outset of a treatment process to enhance the initial rate of microbiological breakdown of the pyritic sulfur content of the coal being treated. This enhancement advantageously lowers the required residence interval of the coal with the culture to achieve improved commerical practicality for the process.

Another method and object of the invention provides a method of reducing the sulfur content of coal by providing an inoculant comprised of a mixture of bacteria compatible with coal under acid conditions and capable of supporting the growth of acidophilic Thiobacilli and acid tolerant heterotrophs as a symbiotic and/or synergistic culture. The coal to be treated is contacted in an aqueous dispersion with the inoculant over an interval effective to substantially reduce the noted sulfur content. Preferably, this contact is carried out in conjunction with a treatment including aeration and agitation.

As another advantageous feature and object of the invention, the noted sulfur reducing biological activity may be carried out within the confines of a coal transporting pipeline in the course of necessary transportation of the coal from one location to another.

An another object and feature of the invention, a method for removing the sulfur content of coal is provided wherein an inoculant comprised of a mixture of bacteria compatible with coal under acid conditions and capble of supporting the growth of acidophilic Thiobacilli and acid tolerant heterotrophs is developed. This inoculant then is contacted with coal in an aqueous dispersion over an interval effective to substantially reduce the sulfur content of the coal. The inoculant may be provided by incubating a quantity of comminuted non-sterile pyrite containing coal with acid coal mine drainage at a pH level and over an interval effective to evoke the growth of the acidophilic Thiobacilli and acid tolerant heterotrophs. Alternatively, the inoculant may be provided by incubating a quantity of the comminuted non-sterile pyrite containing coal over the noted interval and at a selected pH level to promote the growth of the Thiobacilli and heterotrophs. As another approach to developing the inoculant, acid mine drainage may be incubated in combination with a nutrient at a predetermined pH level and over an interval effective to achieve the necessary symbiotic growth of the acidophilic Thiobacilli and acid tolerant heterotrophs.

Other objects of the invention will, in part, be obvious and will, in part, appear hereinafter.

The invention, accordingly, comprises the method possessing the steps which are exemplified in the following detailed disclosure.

For a fuller understanding of the nature and objects of the invention, reference should be had to the following detailed description taken in conjunction with the accompanying drawings.

DETAILED DESCRIPTION

Figure 1:
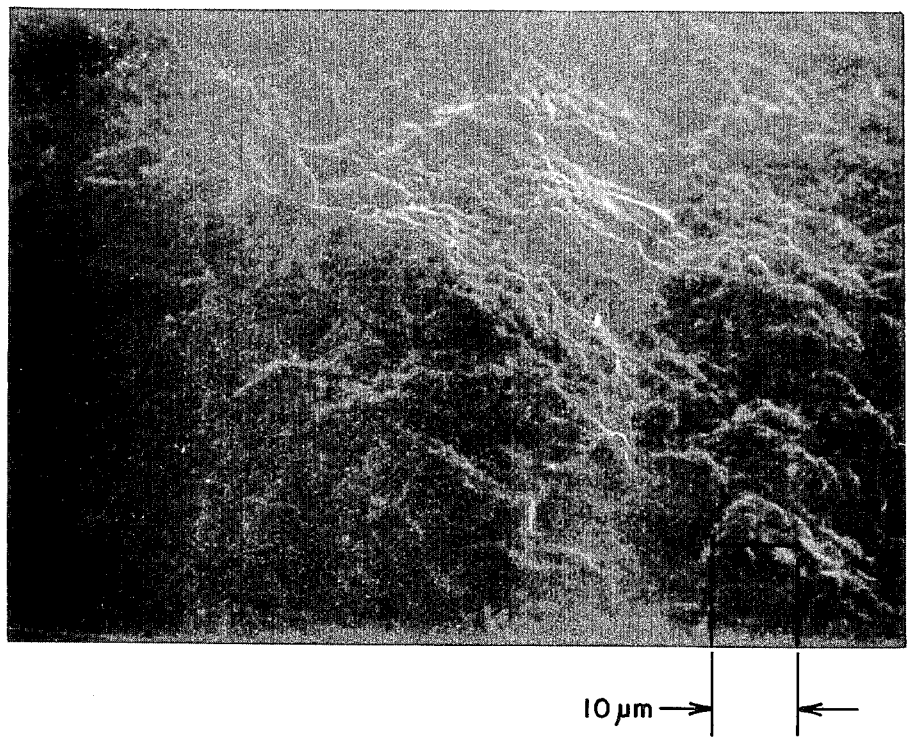
FIG. 1 is a scanning electron micrograph (EM) of a coal refuse sample showing surface porosity.

As the instant description unfolds, it will become apparent that several process factors contribute to the effective removal of pyritic sulfur from coal. Thus, the description initially looks to the microorganisms of highly acidic environments and to enrichment cultures, whereupon it turns to such factors as coal partical size, slurry loading and pH adjustment to stimulate initial culture activites.

In later description herein, it will be observed that certain acidophilic Thiobacilli when utilized alone to remove sulfur from coal and fail to achieve practical removal rates. Among the probable causes of this, the cultures are known to produce autotoxic metabolic by-products, i.e. organic acids, which inhibit iron and sulfur oxidation by the cells when present in sufficient concentration. Accordingly, specific Thiobacilli alone would not be capable of use in isolation to achieve success in process at hand. An enhancement of removal rate is achieved with the process of the instant invention through resort to enrichment cultures incorporating both mixtures of various acid tolerant Thiobacilli and correspondingly mixtures of various acid tolerant heterotrophic microorganisms, the latter being present in amounts effective to act in a symbiotic or synergistic manner with the Thiobacilli.

In general terms, the acidophilic Thiobacilli encountered in the process of the present invention include *T. thiooxidans, T. ferrooxidans, T. acidophilus* and *T. denitrificans.* Heterotrophic microorganisms acting symbiotically or synergistrically with the above will include, inter alia, bacteria, yeasts, filamentous fungi as well as others discussed hereinbelow.

As indicated earlier, under acidic conditions (below pH 4.0) the rate of pyrite oxidation by ferric ions is considerably greater than the rate of ferrous ion oxidation, in the absence of bacteria. Hence, the bacteria catalyze the oxidation of ferrous iron to ferric iron which, in turn, catalyzes the oxidation of pyrite. Thus, bacteria utilized for the instant system serve to catalyze the oxidation of $Fe^{+2}$ to $Fe^{+3}$ to oxidize the pyrite. Consequently, it has been concluded that their catalyzed reaction controls the rate of pyrite oxidation under necessary acidic conditions. See the following publications in this regard:

XVII Singer, P. C., and W. Stumm, Science, 167, 1121 (1970).

XVIII Lau, C. M., K. S. Shumate, and E. E. Smith, Proceed 3rd Symp. on Coal Mine Drainage. Mellon Inst., Pittsburgh, Pa., p 114 (1970).

Looking specifically to *T. ferrooxidans*, while a variety of strains thereof exhibiting varying metabolic capabilities are present in the environment, the microorganism is classified on the basis of its ability to utilize the oxidation of ferrous ion as its sole energy source and $CO_2$ as its sole carbon source. It is placed in the genus Thiobacillus, because it also can oxidize reduced sulfur as a sole energy source. Thus, it is a chemosynthetic autotroph. With respect to its strain variations, *T. ferrooxidans* has been reported to adapt from autotrophic growth on $Fe^{+2}$ to heterotrophic growth on glucose as a carbon and energy source after several transfers in media containing both $Fe^{+2}$ and glucose. See the following publications in this regard:

XIX Remsen, C. C., and D. G. Lundgren, Bacteriol. Proc., 33 (1963).

XX Shafia, F., R. F. Wilkinson, J. Bacteriol., 97, 256 (1969).

XXI Shafia, F., K. R. Brinson, M. W. Heinzman, and J. M Brady, J. Bacteriol., 111. 56 (1972).

XXII Shumate, K. S., E. E. Smith, P. R. Dugan, R. A. Brandt, and C. I. Randles, Rept. U.S. Environ. Protection Agency, Water Poll. Control Ser. DAST-42, 14010 FPR. Washington, D.C. (1971).

Adapted cells contain a complete tricarboxylic acid cycle when grown heterotrophically, but unadapted cells lack alpha-keto glutarate dehydrogenase and reduced nicotinamide adenine dinucleotide oxidase when grown on $Fe^{+2}$, and the presence of $Fe^{+2}$ is reported to repress glucose dissimilation. See the following publication in this regard:

XXIII Tabita, R., and D. G. Lundgren, J. Bacteriol., 108, 328 (1971).

A newer species: T. acidophilus has been suggested as the designation of the facultative heterotrophic bacteria derived from T. ferrooxidans cultures which grow on either organic or reduced sulfur but not on $Fe^{+2}$. See the following publication in this regard:

XXIV Guay, R., and M. Silver, Can. J. Microbiol., 21, 281 (1975).

Differences in enzymes, mole% guanine plus cytosine, 55–57.1% for iron grown and 62.9–63.2% for glucose grown, and lack of the iron oxidizing enzyme in glucose grown cells appear to indicate that heterotrophic isolates are different from autotrophic isolates and that they are selected from T. ferrooxidans cultures. See publications XX, XXI and the following publication in this regard:

XXV Tabita, R., and D. G. Lundgren, J. Bacteriol., 108, 334 (1971).

Additionally, the glucose oxidizing acidophiles have been observed not to react with fluoresceine isothiocyanate labeled rabbit anti- T. ferrooxidans IgG, which is specific for T. ferrooxidans. See the following publication in this regard:

XXVI Apel, W. A., R. R. Dugan, J. A. Filppi, and M. S. Rheins, Appl. Environ, Microbiol., 32, 159 (976).

As indicated earlier, the acidophilic Thiobacilli produce autotoxic metabolic byproducts, i.e. organic acids, which either retard or inhibit metabolism and thus would tend to defeat a microbiological system utilized for the benefication of coal. However, in accordance with the instant invention, enrichment cultures are evolved incorporating acid tolerant heterotrophs which are found in the environments of such acidophilic Thiobacilli. In this regard, reference is made to the following publications:

XXVII Dugan, P. R., and C. I. Randles, Rept. Ohio State Univ. Water Resources Center, Columbus, Ohio, 123 pp. (1968).

XXVIII Dugan, P. R., C. B. Macmillan, and R. M. Pfister, J. Bacteriol, 101, 973 (1970).

XXIX Dugan, P. R., C. B. Macmillan, and R. M. Pfister, J. Bacteriol., 101 982 (1970).

XXX McCoy, B. and P. R. Dugan, In 2nd Symp. on Coal Mine Drainage Research. Mellon Inst., Pittsburgh, Pa., pp. 64–79 (1968).

XXXI Tuttle, J. H., C. I. Randles, and P. R. Dugan, J. Bacteriol., 95, 1495 (1968).

XXXII Tuttle, J. H., P. R. Dugan, C. B. Macmillan, and C. I. Randles, J. Bacteriol., 97, 594 (1969).

Exemplary of said heterotrophs are bacteria, yeasts and molds. An indigenous population of acid tolerant heterotrophic bacteria has been found responsible for the production of slime streamers in highly acid mine water. At least one isolate of the latter group has been identified as having a pH optimum neutrality, as described in connection with publications XXVIII and XXIX supra. Accordingly, it is opined that the organisms colonize in the acid mine streams creating a localized microcosm that is different from the surrounding, highly acid environment. Additional discussion concerning the above will be found in the publications XXVIII and XXIX supra.

Investigators further have reported the growth of a thermophilic mycoplasma, Thermoplasma acidophilum, in refuge piles, reference being made to the following publication:

XXXIII Bohlool, B. B., and T. D. Brock, Appl. Microbiol., 28, 11 (1974).

Yeasts and filamentous fungi frequently have been isolated from acidic mine water, reference being made to publications XXVIII and XXIX, above as well as the following publications:

XXXIV Belly, R. T., and T. D. Brock, J. Bacteriol., 117,726 (1974).

XXXV Cook, W. B., Proc. Indust. Wast. Conf., 21, 258 (1966).

XXXVI Jospeh, J. M., Ohio J. Sci. 53, 123 (1953).

While the source of organic nutrient required to support the rather extensive amount of heterotrophic growth in mine drainage remains speculative, a logical source would be either the metabolic by-products produced by the acidophilic autotrophic growth of T. ferrooxidans or the carbon in coal or both. Several species of algae, especially Euglena and Ulothrix, also have been observed in quantity in acid drainage at pH 3.0 in the presence of sunlight. These algae may either enrich the stream with organic substances or remove by-products that are toxic to the iron and sulfur oxidizers. Other sources of heterotrophic nutrient are available from coal components such as phenolics and the organic content of other sedimentary deposits within coal stratum. Further discourse in connection with the above is provided in publications XXXV and XXXVI above.

Figure 2:
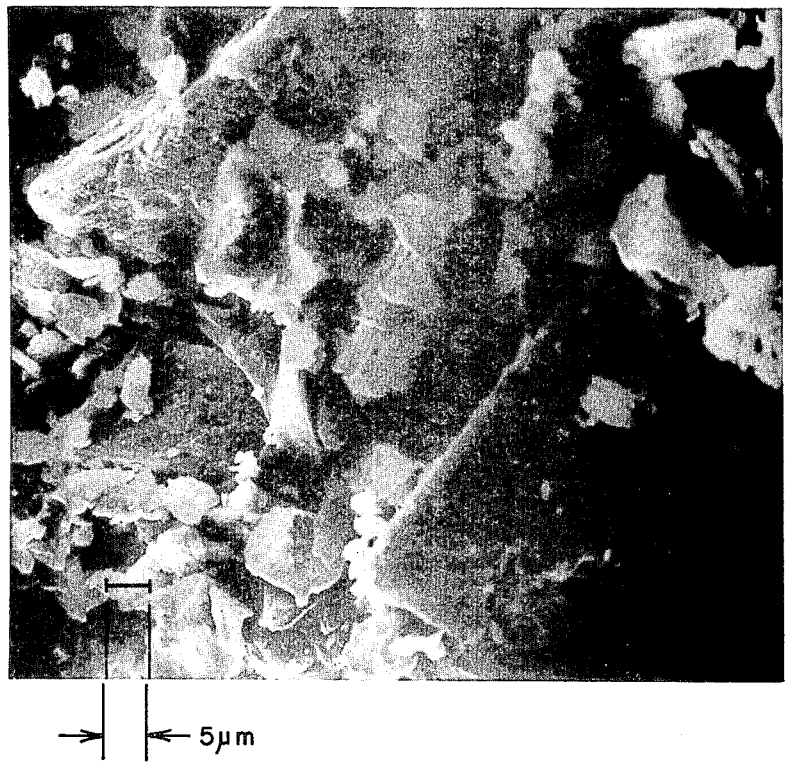
FIG. 2 is another scanning electron micrograph (EM) of pulverized coal sample showing particle structure and what appear to be microbes on the surface thereof.

Inocula utilized in conjunction with the process of the invention are evolved with starting cultures orginating in coal production environments. The selection process deriving successful enriched cultures is one providing an acidic environment as well as nutrients as are made available, inter alia, in the make-up of coal. The finally developed enrichment cultures combine acid tolerant chemosynthetic autotrophs in a symbiotic or synergistic manner with heterotrophs. In the latter regard, it has been shown (supra) that the heterotrophic components of the enrichment cultures may utilize the otherwise debilitating autotoxic organic acid by-products of Thiobacilli. Further however, heterotrophs produce carbon dixoide, vitamins and the like, which, in turn, may act as nutrients to stimulate certain of the acid tolerant autotrophs of the culture to thrive, thus enhancing a symbiotic relationship. It may be noted that the stimulative effect of the overall mixed culture may evoke the pyrite reduction response desired, not only through the enhancement of the growth of certain cultures, but also through an inhibitory action in connection with components otherwise derogating a sulfur reduction function. Refering to FIGS. 1 and 2, scanning electron micrographs (EM) of coal refuse samples showing surface porosity and what may be microorganisms on the surface are revealed. Field studies of the activity of bacteria in such coal refuse have shown a strong correlation between the uptake of carbon dioxide and most probable numbers of iron oxidizing bacteria, but not with the acid tolerant heterotrophic microorganisms also present in the refuse. Utilizing flourescent antibody techniques, *T. ferrooxidans* cells have been detected in the surface washings of such refuse, but none have been detected in refuse which had been prewashed and then pulverized, indicating that *T. ferrooxidans* cells are on the surface of coal refuse but not in the internal pores thereof. Studies of the bacterial growth of samples have shown increases in titratable acidity in non-sterile refuse samples, as compared with acid production over the same period in sterilized refuse control samples. The correlation between acid production rate and growth phase rate of *T. ferrooxidans* in coal refuse suggests that bacteria are the dominant stimulus leading to acid formation from pyrite in coal refuse. In connection with the above, reference is made to the following publication:

XXXVII Apel, W. A., P. R. Dugan, J. A. Filppi, and M. S. Rheins, Appl. Environ, Microbiol., 32, 159 (1976).

Figure 3:
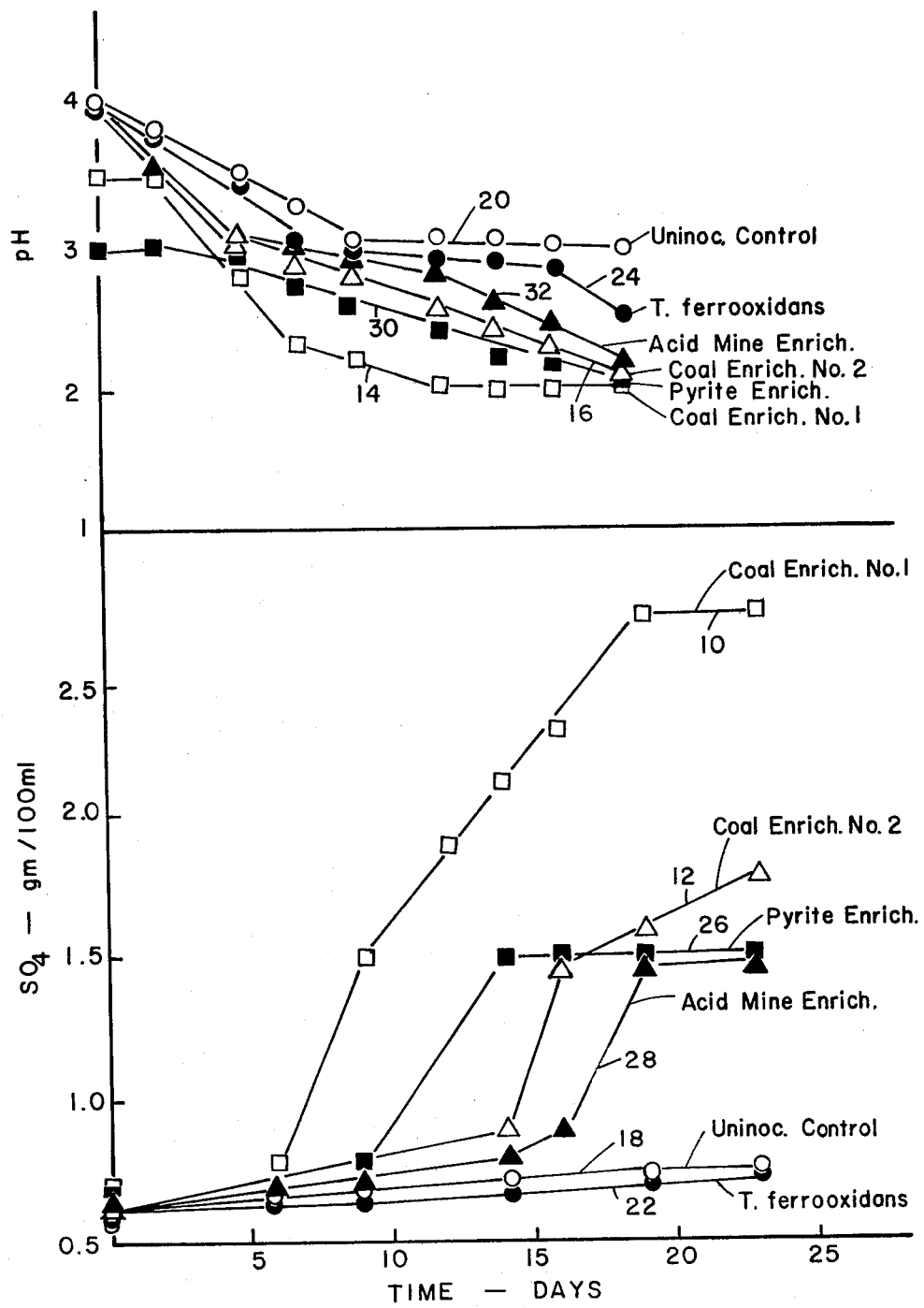
FIG. 3 presents a series of curves showing $SO_4^{-2}$ release from 100-200 mesh partical size coal in aqueous slurry as well as pH change in the presence of various types of inoculum.
Figure 4:
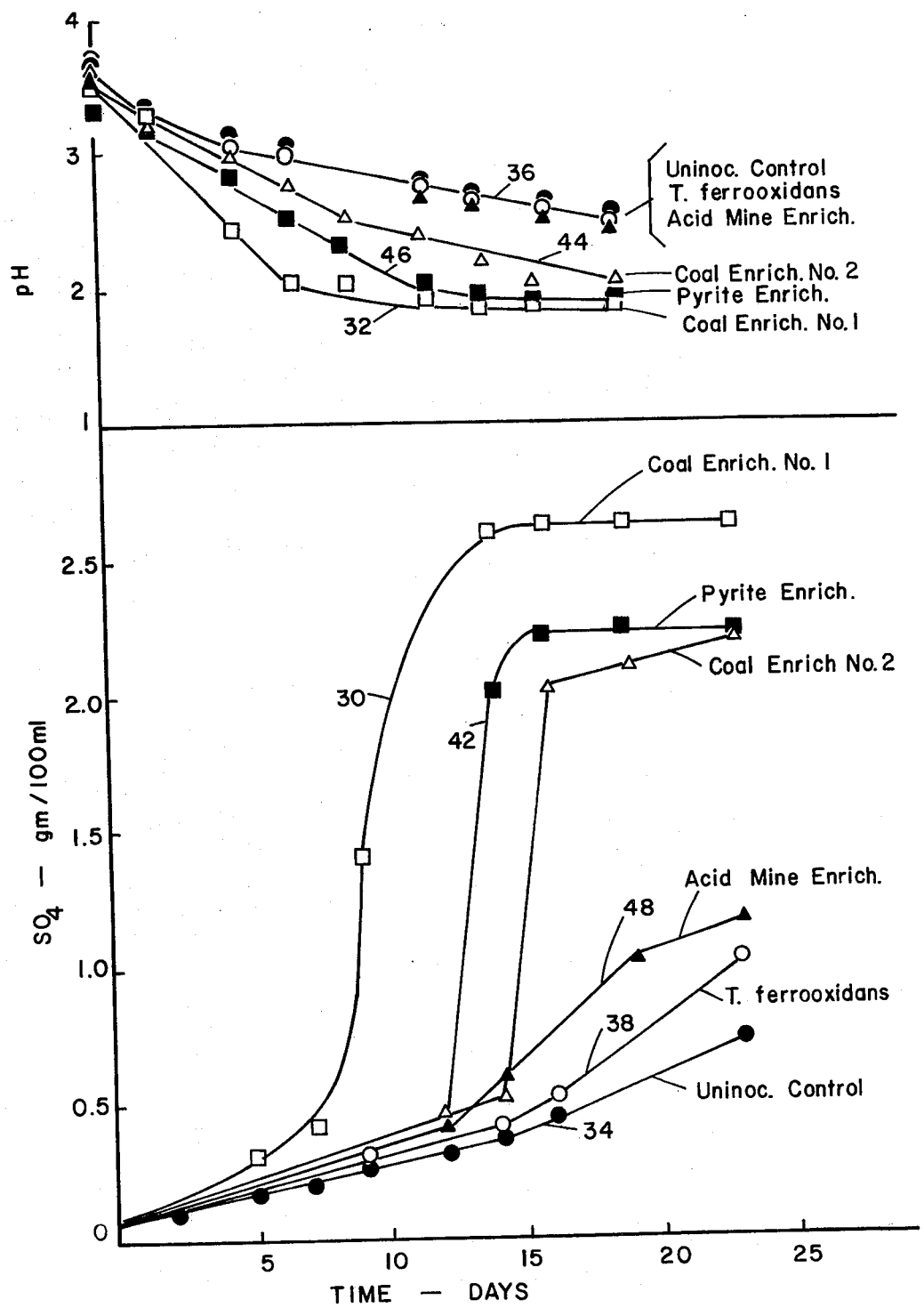
FIG. 4 shows a plurality of curves revealing $SO_4^{-2}$ release from sub 200 mesh particle size coal in aqueous slurries as well as corresponding pH change when in the presence of various types of inoculum.

FIGS. 3 and 4 reveal the activity of enrichment cultures developed in conformance with the method of invention as compared with controls as well as the specific culture, *T. ferrooxidans*. In generating the data shown in these figures, a coal sample was provided representing a power generation station blend of pulverized coal assumed to be a representative sample of commercial coal. This sample was separated into three (3) mesh size fractions and analyzed for total, organic and pyritic sulfur. The results of this analysis are shown below in Table I.

TABLE I

Values Showing % Sulfur Content of Various Fractions of the Pulverized Coal

| Mesh size composition | Sulfur Content as % of Fraction | | | |
|---|---|---|---|---|
| | Total | Pyritic | $SO_4^{-2}$ | Organic |
| 10% 50 to 100 (.297 to .149 mm) | — | — | — | — |
| 45% 100 to 200 (.149 to .974) | 4.2 | 2.9 | 0.1 | 1.2 |
| 45% sub 200 (sub .074 mm) | 5.4 | 4.2 | 0.2 | 1.0 |
| Combined Coal Mixture | 4.6 | 2.1 | 0.1 | 1.4 |

Note from Table I, that about 45% of the pulverized coal sample falls within a 100 to 200 mesh size, while another 45% falls below a 200 mesh size. Select fractions of this coal sample were developed as aqueous slurries in combination with a variety of inocula and the sulfate generating activity of the resultant slurry-borne cultures were observed.

The inocula utilized in the test procedure are labeled in the figures as: Coal Enrichment cultures No. 1 and 2, Pyrite Enrichment, Acid Mine Enrichment and *T. ferrooxidans*. A sterile, uninoculated control sample also is represented in the figures.

Natural coal enrichment culture No. 1 was obtained by inoculating a 10% slurry at pH 3 of non-sterile, ground, high-sulfur coal with acid mine drainage (AMD) and incubating the slurry at ambient temperature (23±2° C.) for four (4) weeks on a gyratory shaker at 200 r.p.m. The acid coal mine drainage components of the slurries were derived from an acid stream (pH 3.5) located approximately ten (10) miles east of McArthur, Ohio.

Coal Enrichment Culture No. 2 was obtained by inoculating a 10% slurry at pH 3 of a non-sterile, ground, high-sulfur coal on a gyratory shaker operating at 200 r.p.m. for four (4) weeks at the noted ambient temperature.

The Pyrite Enrichment inoculum was obtained by combining sulfuric acid (pH 3) and pyrite at the rate of 1 gram pyrite per 100 milliliters of sulfuric acid. To this was added 1 to 5 milliliters of the above described acid mine drainage (AMD). The mixture was held at the noted ambient temperature and shaken at 200 r.p.m. on a gyratory shaker for four (4) weeks.

The acid Mine Enrichment inoculum was developed by combining acid mine drainage and a "9K" basal salts growth medium. This was carried out by adding 1 to 5 milliliters of acid mine drainage (AMD) per 100 milliliters of the "9K" growth solution at pH 3. The "9K" growth medium was provided having the following typical formulation:

| | |
|---|---|
| $(NH_4)_2 SO_4$ | 3.00 g |
| K Cl | 0.1 g |
| $K_2HPO_4$ | 0.5 g |
| $MgSO_4$—7HOH | 0.5 g |
| $Ca(NO_3)_2$ | 0.01 g |
| 10N $H_2SO_4$ | 1.0 ml |
| $FeSO_4$—7HOH* | 44.2 g |
| distilled water to 1 liter | |

*44.2 g $FeSO_4$.7HOH were dissolved in 300 ml water, adjusted to pH 3.5 with $H_2SO_4$ and sterilized separately from the remaining salts contained in 700 ml of acid water. The 2 parts were combined aseptically.

Further information concerning the "9K" growth medium may be obtained in the following publication.

XXXVIII Silverman, M. P., and D. G. Lundgren, J. Bacteriol., 78, 326-331 (1959).

The inoculum was incubated for four (4) weeks on a gyratory shaker at 200 r.p.m. and at the noted ambient temperature.

The specific *T. ferrooxidans* inoculum was grown under forced aeration at ambient temperature (23±2° C.) and with the abovedescribed "9K" growth medium. After five (5) days incubation, the cells were harvested, washed, suspended in (pH 3) $H_2SO_4$ solution, and stored. Suspensions were used as inoculum within one week or less after harvesting.

Looking now to the formation of the coal slurry-culture mixture, fractions of the above described coal sample were formed as 20% slurries (weight to volume) in distilled water. The slurries were adjusted to pH 2.5 with $H_2SO_4$ and 125 ml. aliquots were dispensed in 250 ml. Erlenmeyer flasks and sterilized by autoclaving at 20 psi for 25 minutes. After cooling to ambient temperature, duplicate flasks containing the coal slurries were inoculated with the above-identified inocula, the sterile control remaining uninoculated. Both inoculated and the steril control flasks were placed on a gyratory shaker (200 r.p.m.) and incubated. At 2-3 day intervals during the incubation period, one ml. aliquots were aseptically removed from each of the flasks and used to determine pH and sulfate concentration of the slurries. The pH of each of the samples was determined utilizing a Corning model 12 expanded scale pH meter equipped with a Corning 475060 pH electrode.

The procedure used for the determination of sulfate concentration was a barium sulfate turbimetric procedure in which samples were collected, diluted in water if necessary, and treated with excess $Ba^{+2}$ in the form of $BaCl_2$. The turbidity of each sample was determined in a Shimadsu model MPS-50L multi-purpose scanning spectriphotometer set at a wave length of 450 nm. Percent transmission of each sample was recorded and compared to a standard sulfate curve prepared in the range of 0 to 6000 ppm of sulfate.

Coal slurries which were to be analyzed for total, organic, and pyritic sulfur content following about a 23 day incubation interval were removed from suspension by filtration, washed with distilled water and dried overnight at 40° C., after which the samples were stored in screw-top test tubes and analyzed in accordance with ASTM standards D3177.

The coal fraction utilized in forming the slurries of FIG. 3 contained 100-200 mesh coal. That figure reveals that Coal Enrichment Nos. 1 and 2, as represented at curves 10 and 12, evidenced the highest rate of sulfate release. Note also from the figure, that the corresponding alteration of pH with time for these enrichments, as represented respectively at curves 14 and 16, drops after a period of about 5 to 10 days to a value of about 2.5. Sulfate release data from the sterile uninoculated control slurry are represented at curve 18, while the corresponding pH level exhibited thereby is represented at curve 20. Of particular interest as shown at curve 22, the culture specific to *T. ferrooxidans* utilized in the experiment had essentially no effect on $SO_4^{-2}$ release when compared to release from the sterile uninoculated control represented at curve 18. This supports the noted symbiotic and/or synergistic effect of the enrichment culture process of the invention. The pH level curve corresponding to sulfate release curve 22 is shown at 24.

The sufate release from the Pyrite Enrichment and Acid Mine Enrichment cultures are represented respectively at curves 26 and 28. These curves exhibit sulfate release rates residing somewhat intermediate, thereof, curves 10 and 18. The corresponding pH levels for the slurries represented by curves 26 and 28 are shown respectively at curves 30 and 32. The latter curves again support a positive correlation between acid production with $SO_4^{-2}$ release for the cultures utilized. Subsequent analysis of the coal fraction utilized in developing the data of FIG. 3 showed that with respect to the slurry inoculated with Coal Enrichment No. 1, total pyritic sulfur content, expressed as a percent by weight of the coal fraction, dropped from the 2.9% value shown in Table I to a value of 0.1%.

Looking to FIG. 4, data developed utilizing 20 percent by weight coal slurries prepared in identical fashion with respect to these described above in connection with FIG. 3 but utilizing a smaller particle size coal are revealed. The fraction of the above noted coal sample utilized was that having a particle size which would pass through a 200 mesh sieve. Inoculation procedures for the slurries remained identical to those described in connection with FIG. 3. As is apparent from sulfate release curve 30 for Coal Enrichment No. 1 and its corresponding pH level curve 32, the Coal Enrichment No. 1 continued to evoke a highly effective culture. The $SO_4^{-2}$ rate of release was higher for the case of the smaller particle size coal, as compared with the corresponding curve 10 in FIG. 3. Data developed from the uninoculated control slurry are represented at curves 34 and 36, and respectively show low sulfate removal as well a relatively low rate of pH value decline, as would be expected. That slurry inoculated specifically with *T. ferrooxidans* and not with an enrichment culture performed as represented at sulfate removal curve 38. As in the case of the corresponding data in FIG. 3, the rate of sulfate removal is very low for that inoculum as compared with the enrichment cultures. The pH removal curve for this culture is identified as the earlier described curve 36, inasmuch as essentially all data points for the control, *T. ferrooxidans* culture and the Acid Mine Enrichment culture fell somewhat congruently.

The slurry inoculated with Coal Enrichment No. 2 as well as the Pyrite Enriched slurry derived cultures evidencing relatively high rates of sulfate removal at respective curves 40 and 42 for the smaller particle size fraction. Similiarly, the corresponding pH levels, plotted at respective curves 44 and 46, show a relatively enhanced acid production in correlation with the higher rate of sulfate release. The Acid Mine Enriched slurry provided a sulfate release, as represented at curve 48, slightly lower than the corresponding curve 28 in FIG. 3, while the corresponding pH level plot is represented, as indicated earlier, at common curve 36. As represented in Table I, the initial pyritic sulfur content for the passing a 200 mesh sieve represented 4.2 percent by weight of that fraction treated utilizing Coal Enrichment No. 1 inoculum and discussed in connection with curves 30 and 32. This pyritic sulfur percentage dropped to 0.5 percent by weight at the termination of treatment with the inoculated culture.

Figure 5:
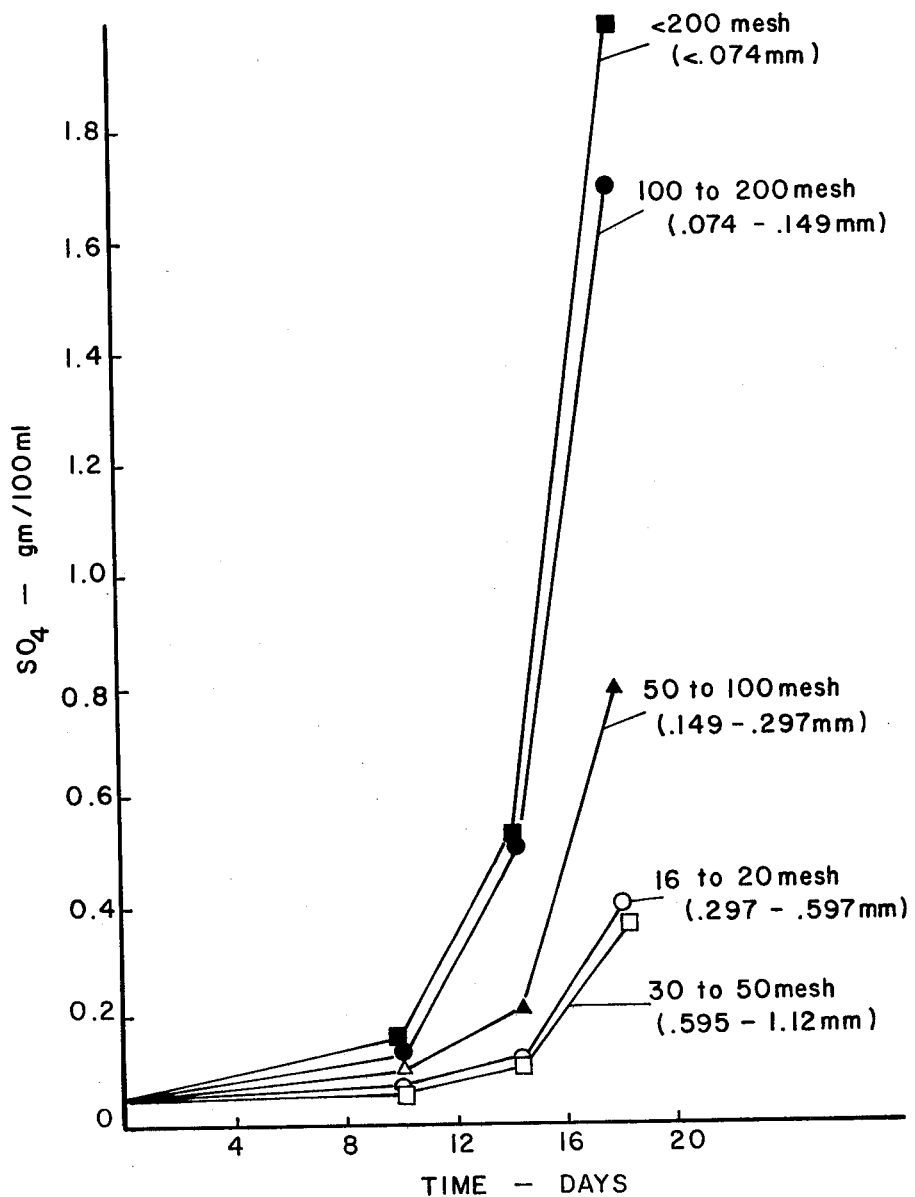
FIG. 5 presents a series of curves showing relative rates of $SO_4^{-2}$ release from various particle sizes of coal retained within slurries in the presence of an enrichment culture.

A comparison of the above discussed curves set forth in FIGS. 3 and 4 provides an indication that the rate of sulfate removal on the part of the culture is enhanced as a particle size of the coal fraction diminishes. Because of the factor involved in the natural evolution of coal itself wherein a myriad of former life forms have evolved into coal strata, the location of sulfur components varies considerably within any given region. This variation also applies to the size of the sulfur components as evidenced when the total sulfur content of a given coal sample is analyzed as represented, for example, in Table I. Note in that table, that the fractions exhibiting smaller particle sizes also exhibit a higher relative sulfur content. In effect, as the particle size diminishes, more pyritic sulfur becomes available to the microbiological reaction process. FIG. 5 reveals this to be the case in connection with the rate of sulfate removal. The curves as labeled in that figure were developed utilizing fractions of varying coal particle size inoculated with a coal enrichment inoculum similiar to that described above as Coal Enrichment No. 1. Similar to the procedure deriving data for FIGS. 3 and 4, the slurries developing the data generating the curves of FIG. 5 were agitated at 25°±2° C. in the presence of the noted enrichment culture. It may be observed from the figure that higher rates of sulfate removal are achieved with smaller particle sizes. Thus, the process of the invention favors the utilization of such smaller sizes from the standpoint of lowering the requisite processesing interval for achieving requisite low sulfur levels.

The degree or extent of slurry loading with coal also will be found to have an effect upon the rate of sulfate removal. This effect is revealed in connection with the curves of FIGS. 6 and 7 taken in conjunction with the data set forth below in Table II. Data Developing the curves of FIGS. 6 and 7 were generated utilizing a series of five discrete aqueous slurry loadings with coal exhibiting a particle size distribution substantially similar to that shown in Table I above. The slurries were prepared having by weight coal loadings of 10%, 20%, 30% 40% and 50% in distilled water, were adjusted to pH 2.5 with 10N $H_2SO_4$ and 125 ml. aliquots were dispersed in 250 ml. Erlenmeyer flasks and sterilized by autoclaving at 20 p.s.i. for 25 minutes. After cooling to ambient temperature, duplicate flasks containing each of the above slurries were inoculated with 5% inoculum from Coal Enrichment culture No. 1 described above, while two more flasks from each of the above slurries remained uninoculated and served as sterile controls. Both inoculated and sterile flasks were placed on a gyratory shaker and agitated at 200 r.p.m. over an incubation period of 14 days at 23±2 C. At two to three day intervals during the incubation period, 1 ml. aliquots were aseptically removed from each of the flasks and used to determine pH and sulfate concentration of the slurries. The procedure used for the determination of sulfate concentration was a modification of the Barium sulfate turbimetric procedure as described hereinabove. Coal slurries that were to be analyzed for total, organic, and pyritic sulfur were removed from suspension by filtration,, washed with distilled water and dried overnight at 40° C., after which the samples were stored in screw-top test tubes and analyzed under ASTM standard D3177. The curves shown in FIG. 7 additionally were provided a microbial supplementary nutrient, present as an addition of 0.3% weight per water volume of $(NH_4)_2SO_4$.

Figure 6:
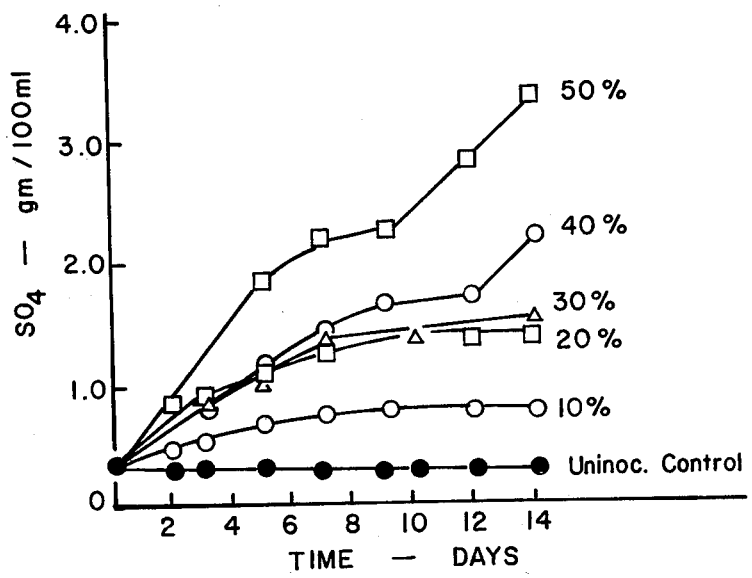
FIG. 6 presents a series of curves showing $SO_4^{-2}$ release from various percent aqueous slurries of pulverized coal as inoculated with an enrichment culture of bacteria.
Figure 7:
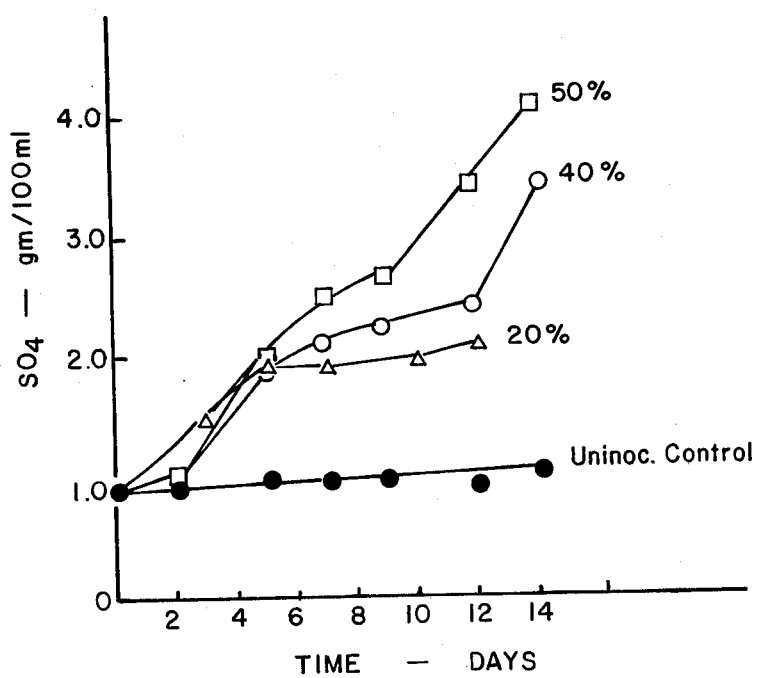
FIG. 7 shows a series of curves revealing $SO_4^{-2}$ release from various percent aqueous slurries of a pulverized coal blend when inoculated with an enrichment culture combined with a 0.3% $(NH_4)_2SO_4$ supplemental nutrient.

The labeled curves in each of FIGS. 6 and 7 show that the rate of sulfate production will vary with slurry loading. However, Table II below shows that a more thorough pyritic sulfur removal may be achieved with lower slurry loading although more total sulfur is removed from the higher slurry loading over a specified time interval.

Figure 8:
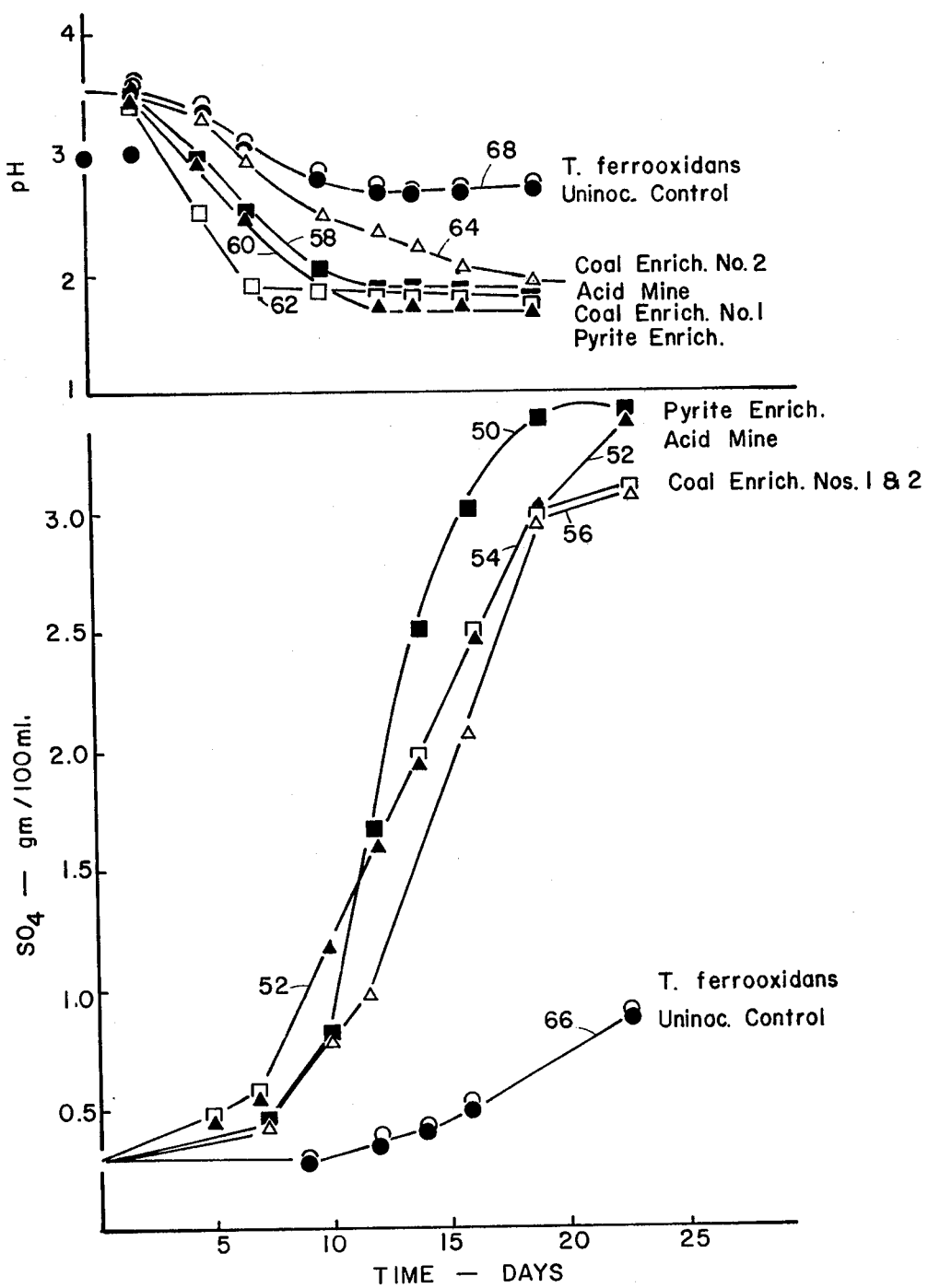
FIG. 8 presents a series of curves showing $SO_4^{-2}$ release and corresponding pH change from coal particle slurries of less than 200 mesh size as supplemented with a basal salt solution and in the presence of various types of inoculum.

The results of monitering pH and sulfate levels, as described hereinabove, are presented in FIG. 8. Looking to the curves therein, it may be observed that the slurries inoculated with Pyrite Enrichment cultures, Acid Mine Enrichment cultures, Coal Enrichments No. 1 and 2, as revealed respectively by curves 50, 52, 54 and 56, evidenced relatively high rates of sulfate removal. In particular, these rates are higher than those represented in FIGS. 3 and 4. The corresponding lowering of pH as represented by respective curves 58, 60, 62 and 64 also show a relatively higher rate of acid development. Note additionally, that the congruent curves at 66 representing the uninoculated control slurry as well as that slurry inoculated with *T. ferrooxidans* remain low as did the extent of pH change corresponding thereto at curve 68. The lag period, however, was not significantly reduced.

A collective observation of the pH data in FIGS. 3, 4 and 8 reveals that a rapid release of $SO_4^{-2}$ is witnessed after the corresponding pH values dropped below 2.5. Similarly, the highest rates of sulfate release are observed within a corresponding pH range of values between about 1.5 and 2.8. This suggests that the pyrite oxidizers are most active within such range. Accordingly, an investigation was carried out wherein each of the slurries were initially adjusted to a variety of pH values. Also, experiments have shown that the optimum pH for iron oxidation by one strain of *T. ferrooxidans* resides in the range of about 2.3 to 2.8 with a somewhat

TABLE II

| | Total S | Pyritic S | Organic S | $SO_4^{-2}$ | Gm Coal/ flask | Total Gm S removed/ flask |
|---|---|---|---|---|---|---|
| Starting Coal Blend | 4.6 | 3.1 | 1.4 | 0.2 | — | — |
| After 14 day microbial treatment | | | | | | |
| 30% slurry | 2.0 | 0.6 | 1.2 | 0.2 | 37.5 | 0.97 |
| 40% slurry | 2.6 | 1.0 | 1.4 | 0.2 | 50.0 | 1.00 |
| 50% slurry | 3.0 | 1.4 | 1.5 | 0.2 | 72.5 | 1.16 |
| 50% + $(NH_4)_2SO_4$ | 2.9 | 1.1 | 1.5 | 0.3 | 72.5 | 1.23 |

FIGS. 6 and 7 additionally support that aspect of the invention concerning flexibility in the types of procedures available for carrying out pyritic sulfur removal. They may vary considerably to meet the needs of a particular installation. For example, the aqueous cultures may be used in conjunction with leaching, beds in aeration tanks or oxidation ponds. A particularly advantageous approach to the use of the culture containing slurries is in connection with coal transporting pipe lines or similar liquid conveyance arrangements. For example, the coal can be reacting with the sulfur removing cultures while in transit within a pipeline. Thus, holding periods otherwise required for carrying out sulfur removal essentially are eliminated to improve the economics associated with coal benefication.

An examination of FIGS. 3 and 4 reveals a lag or delay interval of about 6 or 7 days before the rate of $SO_4^{-2}$ removal achieves relatively high values. To improve the practicality of the process at hand, it is desirable that this lag interval be minimized. In one attempt to reduce this lag period, a series of the earlier-described 20% slurries of sub 200 mesh particle size coal were supplemented with the "9K" basal salts described above. Techniques for providing the slurries and inoculum were identical to those described in connection with FIGS. 3 and 4.

drastic reduction of iron oxidation where such value falls below a pH level of 2.0 or above a level of 3.5. This earlier effort will be seen to be somewhat consistent with the data now disclosed.

Figure 9:
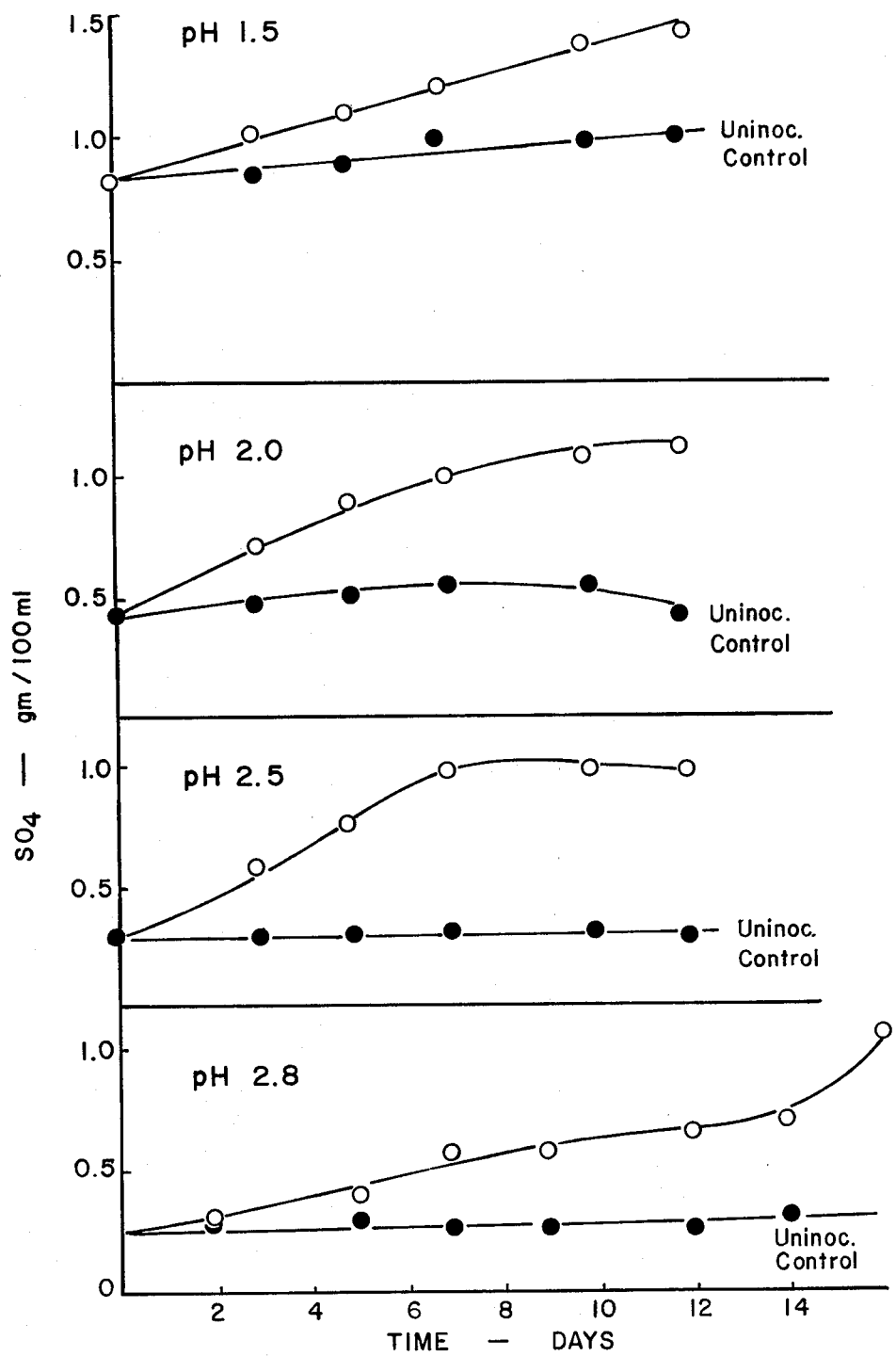
FIG. 9 presents a series of curves showing a variation in lag intervals for $SO_4^{-2}$ release as influenced by initial pH adjustment of inoculated 20% aqueous slurries of coal.

Looking to FIG. 9, the sulfate release rate for 20% (weight to volume) slurries of coal exhibiting the particle size blend represented in Table I and inoculated with Coal Enrichment No. 1 in the manner described in connection with FIGS. 3 and 4 are shown. However, the pH of the slurries as initially formed were varied as represented in the figure. Monitoring of the sulfate release rates shows that the above-noted lag period is significantly reduced where the initial pH value of the slurries is adjusted to fall within the range of values of about 1.5 to 2.8 and particularly, between 2.0 and 2.5. As is apparent, the curves are shown in combination with uninoculated control slurries.

With verification of the value of an initial pH adjustment to the slurries, the investigation then looked to the effect on lag period of the addition of supplemental nutrients. Accordingly, 20% (weight to volume) slurries of the above-noted coal sample shown in Table I were inoculated with Coal Enrichment No. 1 and the slurries were adjusted to exhibit an initial pH value of 2.5. Supplemental nutrients added were: the earlier described "9K" salts; the earlier described 0.3%

Figure 10:
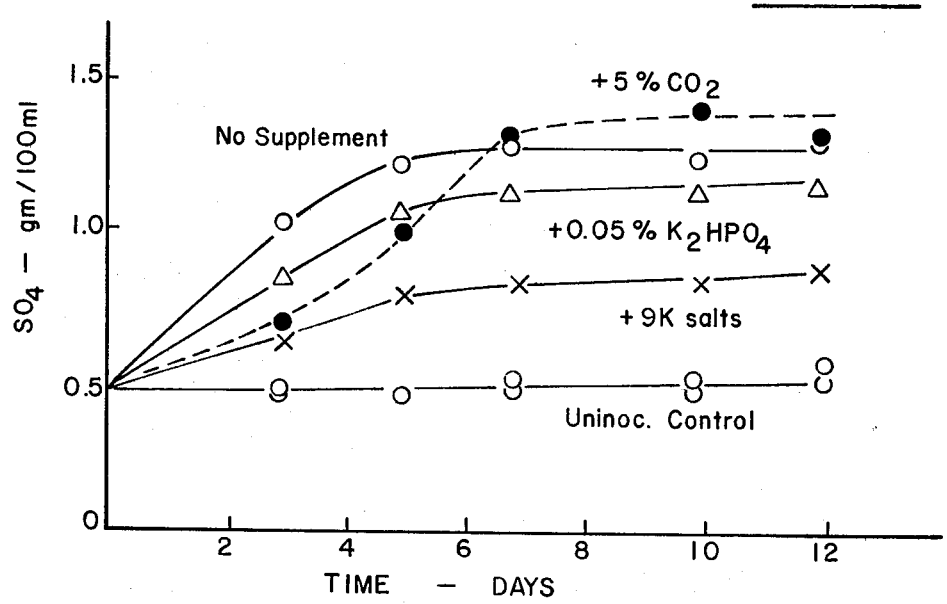
FIG. 10 presents a series of curves showing $SO_4^{-2}$ release from inoculated 20% aqueous coal slurries initially adjusted to pH 2.5 and with and without various supplemental nutrients.
Figure 11:
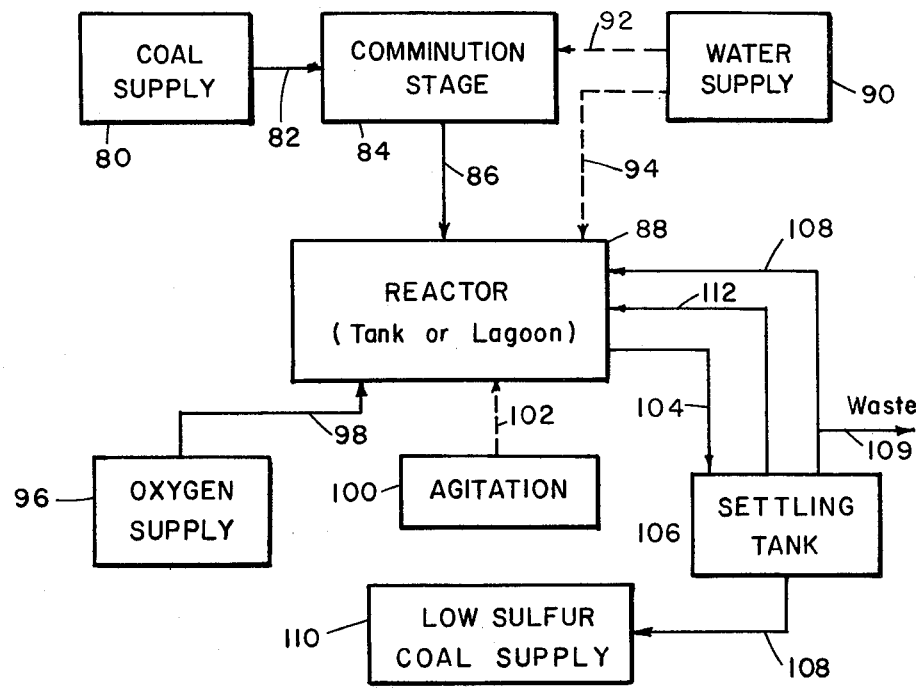

$(NH_4)_2SO_4$; and 0.05% $K_2HPO_4$. Additionally, a 5% addition of $CO_2$ within the head space of a control growth chamber was provided for one sample. The data developed by monitoring sulfate release observable for the slurries are represented in FIG. 10 and reveal that no increase in the rate of sulfate release is achieved. The addition of the 5 percent $CO_2$ as a gas in the head space of a control growth chamber is seen to result initially in an increased lag. This increased lag possibly exists as a result of a buffering of the pH level to above the optimum pH followed by a slight positive effect on sulfate release. The figure also reveals that the addition of 0.3% $(NH_4)_2SO_4$ had a beneficial influence on both the rate and amount of sulfate release.

Throughout the discussion above, an "ambient" temperature has been described as being used in developing the sulfate-removal data shown in the figures. In the course of the investigation leading to the instant invention, it was found that a temperature range of about 20° C. to 35° C. is available for the process, no net acceleration of sulfate release being observed either with temperature increase or decrease within that range.

As indicated earlier herein, the practical applications of the method of the invention or the benefication of coal are many-fold. For most applications, the process utilized will be one continuous in nature wherein coal is continuously fed into a reactor and continuously removed therefrom as low-sulfur coal following an appropriate residence interval. In the system, acid liquid which contains microbes is continuously drawn off and recirculated as an enrichment inoculant for treating freshly arriving coal.

Figure 11:
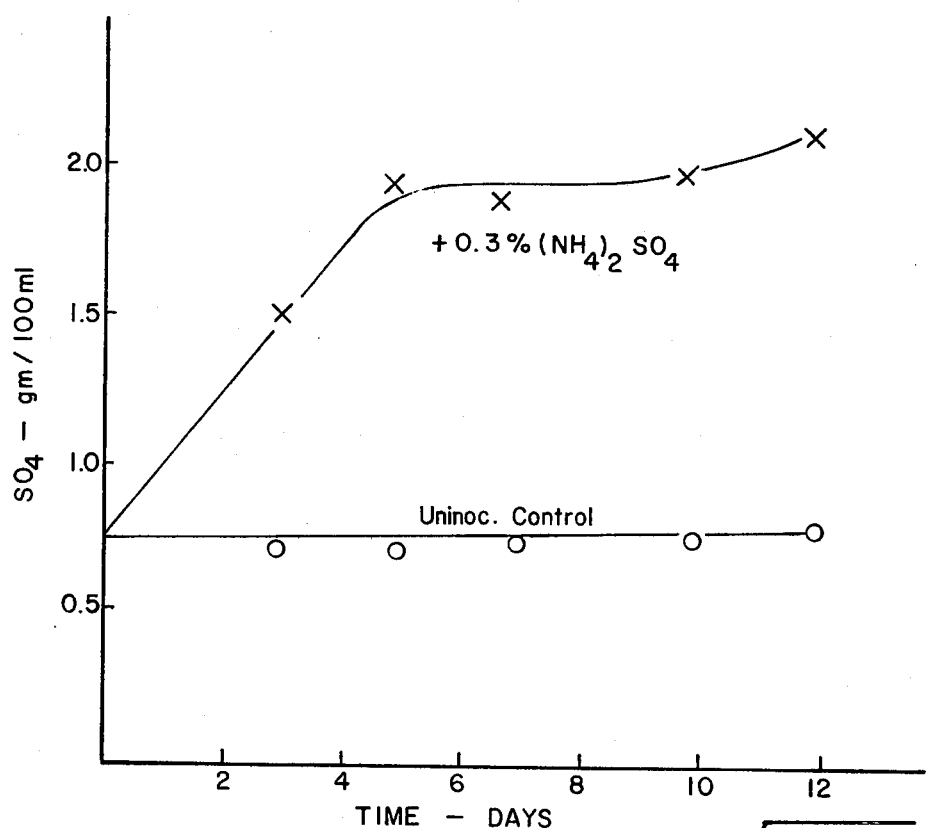
FIG. 11 is a block flow diagram of one coal benefication process according to the invention.

Looking to FIG. 11, a block schematic flow diagram for such a process is represented. FIG. 11 shows a coal supply at 80 being delivered, as represented by line 82, to a comminution stage 84. At stage 84, the desired coal particle size is derived for introduction, depicted by line 86, into a reactor, represented at block 88. Water plays an important role in the process and the supply thereof is represented at block 90. From block 90, water alternately may be supplied at the comminution stage 84, as represented by dashed line 92, may be introduced at reactor stage 88, as represented at line 94, or may be the carrier component utilized in piping the coal supply to reactor 88.

Within reactor 88, oxygen, for example, in the form of air is supplied from a source represented by block 96 and introduced to reactor 88 by mechanisms represented generally by line 98. Such mechanisms would include compressors combined with perforated pipes or the like. In addition to the provision of oxygen from supply 96, the coal slurry within reactor 88 preferably is agitated as represented by block 100 and dashed connection 102. As is apparent, for certain applications, the introduction of the oxygen from line 98 may supply adequate agitation. Reactor 88 may be present as a tank or lagoon and, following a predetermined residence interval selected for sulfur reduction, liquid-borne treated coal may be removed therefrom as indicated by line 104 to a settling tank represented by block 106. Within tank 106, supernatent liquid developed at the uppermost regions thereof which contains inoculant is reintroduced to reactor 88 through conduits as represented by line 108. However, inasmuch as an excess of the supernatant liquid normally will be encountered, a portion thereof is committed to waste as indicated by line 109. Treated coal is removed from settling tank 106 as indicated by line 108 for delivery as a low-sulfur coal supply represented by block 110. In addition to the removal of supernatent inoculant as represented by line 108, coal-borne inoculant may be removed from settling tank 106 and recirculated to reactor 188, as represented by line 112.

Figure 12:
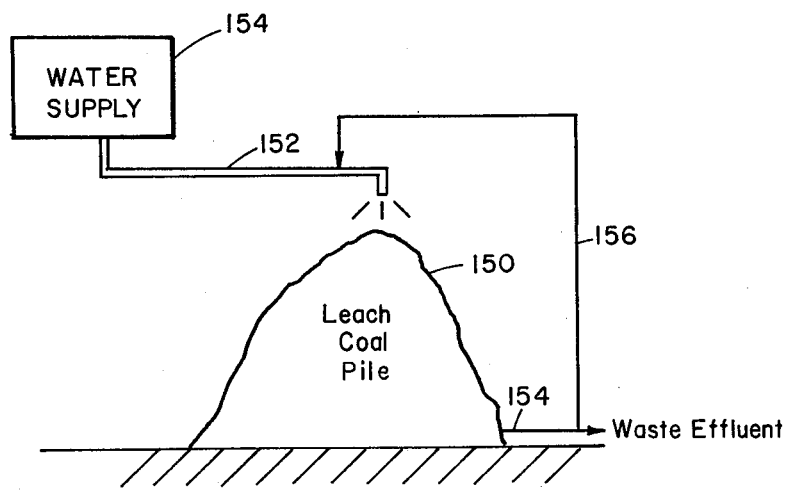
FIG. 12 is a schematic representation of another coal benefication process according to the invention.

Looking to FIG. 12, a more basic approach to the treatment of high-sulfur coal is schematically represented. In this diagram, a coal pile represented at 150 is treated by soaking it from the nozzle of a conduit 152 coupled with a water supply represented by block 154. The sulfur-reducing cultures evolve as the water leaches through coal pile 150 and are withdrawn from the waste fluids issuing therefrom at 154 and, as represented by line 156, are added to the water supply passing through conduit 152. Thus, an inexpensive arrangement for removing sulfur from coal is provided.

Since certain changes may be made in the above-described method without departing from the scope of invention herein involved, it is intended that all matter contained in the above description or shown in the accompanying drawings shall be interpreted as illustrative and not in a limiting sense.

What is claimed is:

1. A method for reducing the pyritic sulfur content of coal comprising the steps of:
   providing an inoculant comprised of a mixture of autotrophic *acidophilic Thiobacilli* and acid tolerant heterotrophic microorganisms, said heterotrophic microorganisms derived from cultures originating in coal-bearing environments from where coal is produced, said Thiobacilli and said heterotrophic microorganisms being cultured under acidic conditions for enrichment so as to provide said inoculant with said Thiobacilli and heterotrophic microorganisms in an amount effective to evoke substantial reduction of the sulfur content of said coal; and
   contacting said coal in comminuted form with an aqueous dispersion of said inoculant under conditions effective to substantially reduce the sulfur content thereof.

2. The method of claim 1 including the step of comminuting said coal to exhibit a particle size less than about 0.3 mm prior to the contact thereof with said aqueous dispersion.

3. The method of claim 2 in which a substantial portion of said coal is comminuted to exhibit a particle size passing a 200 mesh sieve.

4. The method of claim 1 wherein said inoculant is provided by incubating in the presence of water a quantity of comminuted non-sterile pyrite containing coal with acid coal mine drainage at a pH level and over a interval effective to evoke the growth of said autotrophic acidophilic Thiobacilli and acid tolerant heterotrophs.

5. The method of claim 1 wherein said aqueous dispersion exhibits a pH value within the range of about 1.5 to 2.8 upon the initial contact thereof with said coal.

6. The method of claim 1 wherein said step of contacting said coal with said aqueous dispersion is carried out within a coal transporting pipeline.

7. The method of claim 1 wherein said Thiobacilli includes *T. ferrooxidans*.

8. The method of claim 1 wherein said Thiobacilli includes *T. thiooxidans*.

9. The method of claim 1 wherein said Thiobacilli includes *T. acidophilus*.

10. The method of claim 1 including the step of providing stimulatory nutrients with said aqueous dispersion.

11. The method of claim 1 wherein said inoculant is provided by incubating in the presence of water a quantity of pyrite with acid coal mine drainage at a pH level and over an interval effective to evoke the growth of said autotrophic acidophilic Thiobacilli and said acid tolerant heterotrophs.

12. The method of claim 1 wherein said inoculant is provided by incubating acid mine drainage and nutrient at a pH level and over an interval effective to evoke the growth of said autotrophic acidophilic Thiobacilli and acid tolerant heterotrophs.

13. The method of claim 1 wherein said inoculant is provided by incubating an aqueous dispersion of comminuted, non-sterile, pyrite containing coal at a pH level and over an interval effective to evoke the growth of said autotrophic acidophilic Thiobacilli and acid tolerant heterotrophs.

14. A method for reducing the pyrite sulfur content of coal comprising the steps of:
    comminuting the coal to exhibit a particle size distribution effective for exposing said sulfur content to an extent sufficient to support microorganism growth; and
    contacting said comminuted coal with an enrichment culture which contains autotrophic acid tolerant Thiobacilli species in combination with acid tolerant heterotrophic microorganisms under conditions effective to substantially reduce the sulfur content thereof, said heterotrophic microorganisms derived from cultures originating in coal-bearing environments from where coal is produced, said Thiobacilli and said heterotrophic microorganisms being cultured under acidic conditions for enrichment so as to provide said enrichment culture with said Thiobacilli and heterotrophic microorganisms in an amount effective to evoke the reduction of the sulfur content of said coal.

15. The method of claim 14 wherein said comminuted coal is contacted with an aqueous dispersion of said enrichment culture having a pH value between about 1.8 to 3.5.

16. The method of claim 14 wherein said enrichment culture is provided by incubating an aqueous dispersion of comminuted, non-sterile pyrite containing coal with said coal mine drainage at a pH level and over an interval effective to evoke the growth of said autotrophic acid tolerant Thiobacilli and acid tolerant heterotrophs.

17. The method of claim 16 wherein said pH level of said aqueous dispersion is selected between about 1.8 and 3.8.

18. The method of claim 14 wherein said enrichment culture is provided by incubating an aqueous dispersion of pyrite and acid coal mine drainage at a pH level and over an interval of time effective to evoke the growth of said autotrophic acidophilic Thiobacilli and acid tolerant heterotrophs.

19. The method of claim 14 wherein said enrichment culture is provided by incubating acid mine drainage and nutrient at a pH level and over an interval effective to evoke the growth of said autotrophic tolerant Thiobacilli and acid tolerant heterotrophs.

20. The method of claim 14 wherein said enrichment culture is provided by incubating an aqueous dispersion of comminuted non-sterile pyrite containing coal at a pH level and over an interval effective to evoke the growth of said autotrophic acid tolerant Thiobacilli and acid tolerant heterotrophs.

21. The method of claim 14 wherein said Thiobacilli includes *T. ferrooxidans*.

22. The method of claim 14 wherein said Thiobacilli includes *T. thiooxidans*.

23. The method of claim 14 wherein said Thiobacilli includes *T. acidophilus*.

24. The method of claim 14 in which said acid tolerant heterotrophs comprise bacteria, yeasts and molds.

25. The method of claim 14 wherein said step of contacting said comminuted coal with said enrichment culture is carried out within a coal transporting pipeline.

26. A method for reducing the pyrite sulfur content of coal comprising the steps of:
    introducing said coal into a reactor as a slurry with water, said reactor containing an enrichment culture which includes autotrophic acidophilic Thiobacilli species in combination with acid tolerant heterotrophic microorganisms, said heterotrophic microorganisms derived from cultures originating in coal-bearing environments from where coal is produced, said Thiobacilli and said heterotrophic microorganisms being cultured under acidic conditions for enrichment so as to provide said enrichment culture with said Thiobacillis and heterotrophic microorganisms in an amount effective to evoke the substantial diminishment of the pyritic sulfur content of said coal;
    passing oxygen-laden gas through said slurry within said reactor;
    removing liquid-borne coal from said reactor following an interval effective to substantially diminish the pyritic sulfur content thereof;
    removing said liquid from said liquid-borne coal; and
    returning at least a portion of said removed liquid to said reactor to provide inoculum for said enriched culture.

27. The method of claim 26 including the step of agitating said coal and water slurry within said reactor.

* * * * *

UNITED STATES PATENT OFFICE
CERTIFICATE OF CORRECTION

Patent No. 4,456,688     Dated June 26, 1984

Inventor(s) Patrick R. Dugan

It is certified that error appears in the above-identified patent and that said Letters Patent are hereby corrected as shown below:

On the title page of the patent, the inventor should read:
--- Patrick R. Dugan (sole inventor)---;

On the abstract page, in line 5, "Hetrotrophic" should read --- Heterotrophic ---;  and in line 6-7, "symbotic" should read --- symbiotic ---;

In column 2, line 26, "publictions" should read --- publications ---;

In column 3, line 23, "comcomitant" should read -- concomitant --;

In column 3, line 44, "set fourth" should read --- set forth ---;

In column 5, line 31, "partical" should read --- particle ---;

In column 5, lines 65-66, "benefication" should read --- beneficiation ---;

In column 5, line 68, "benefication" should read --- beneficiation ---;

In column 6, line 8, "partical" should read --- particle ---;

In column 7, line 46, "benefication" should read --- beneficiation ---;

In column 8, line 13, "refuge" should read --- refuse ---;

UNITED STATES PATENT OFFICE
CERTIFICATE OF CORRECTION

Patent No. 4,456,688          Dated June 26, 1984

Inventor(s) Patrick R. Dugan

It is certified that error appears in the above-identified patent and that said Letters Patent are hereby corrected as shown below:

In Column 9, line 4, "flourescent" should read --- fluorescent ---;

In column 10, line 54, "steril" should read --- sterile ---;

In column 10, line 63, "turbimetric" should read --- turbometric ---;

In column 10, line 68, "spectriphotometer" should read --- spectrophotometer ---;

In column 11, lines 61-62, "as well a relatively" should read --- as well as a relatively ---;

In column 13, line 13, "turbimetric" should read --- turbometric ---;

In column 13, line 57, "benefication" should read --- beneficiation ---;

In column 15, line 24, "benefication" should read --- beneficiation ---;

In column 16, line 4, "r eactor 188" should read --- reactor 88 ---.

Signed and Sealed this

Second Day of April 1985

[SEAL]

Attest:

DONALD J. QUIGG

*Attesting Officer*      *Acting Commissioner of Patents and Trademarks*